(12) United States Patent
Decock et al.

(10) Patent No.: US 11,242,181 B2
(45) Date of Patent: Feb. 8, 2022

(54) LIQUID DISPENSING DEVICE

(71) Applicant: Nemera La Verpillière S.A.S., La Verpilliere (FR)

(72) Inventors: Thierry Decock, Lyons (FR); Benjamin Quaglia, Lyons (FR); Gaëtan Painchaud, Francheville (FR)

(73) Assignee: Nemera La Verpillière

( * ) Notice: Subject to any disclaimer, the term of this patent is extended or adjusted under 35 U.S.C. 154(b) by 22 days.

(21) Appl. No.: 15/301,606

(22) PCT Filed: Mar. 27, 2015

(86) PCT No.: PCT/FR2015/050796
§ 371 (c)(1),
(2) Date: Oct. 3, 2016

(87) PCT Pub. No.: WO2015/150673
PCT Pub. Date: Oct. 8, 2015

(65) Prior Publication Data
US 2017/0029175 A1    Feb. 2, 2017

(30) Foreign Application Priority Data

Apr. 2, 2014 (FR) ...................... 1452902

(51) Int. Cl.
*B65D 47/18*   (2006.01)
*B65D 1/02*    (2006.01)
(Continued)

(52) U.S. Cl.
CPC ............ *B65D 47/18* (2013.01); *A61J 1/05* (2013.01); *B65D 1/023* (2013.01); *B65D 1/0246* (2013.01);
(Continued)

(58) Field of Classification Search
CPC .... B65D 47/18; B65D 41/0414; B65D 1/023; B65D 1/0246; B65D 1/0223
(Continued)

(56) References Cited

U.S. PATENT DOCUMENTS 2,526,225 A    10/1950   Gronemeyer et al.
2,742,195 A     4/1956   Elder, Jr.
(Continued)

FOREIGN PATENT DOCUMENTS

BE    648227 A     11/1964
BE    750714 A1    11/1970
(Continued)

OTHER PUBLICATIONS

Office Action from European Patent Office for Application No. 15717570.4-1009 dated Jun. 7, 2021 (9 pages).

*Primary Examiner* — Don M Anderson
(74) *Attorney, Agent, or Firm* — St. Onge Steward Johnston & Reens LLC

(57) ABSTRACT

A liquid dispensing device includes a dispensing end piece and a neck of a reservoir for storing the liquid, the end piece being attached to the neck, which has a tubular internal surface. The end piece has a tubular internal skirt that is mounted in the neck and defines, with the internal surface, at least one annular sealing zone, preventing the liquid from passing between the internal skirt and the neck. The skirt defines, with the internal surface, a separate zone for retaining shavings, which prevents shavings that are formed in the sealing zone while the end piece is being fitted into the neck from getting into the reservoir.

14 Claims, 5 Drawing Sheets

(51) Int. Cl.
    *B65D 41/04*     (2006.01)
    *B65D 47/20*     (2006.01)
    *A61J 1/05*     (2006.01)
    *A61F 9/00*     (2006.01)

(52) U.S. Cl.
    CPC ..... *B65D 41/0414* (2013.01); *B65D 47/2081* (2013.01); *A61F 9/0008* (2013.01)

(58) Field of Classification Search
    USPC .......................... 215/320, 321, 356, 318, 344
    See application file for complete search history.

(56) References Cited

U.S. PATENT DOCUMENTS

| | | | |
|---|---|---|---|
| 3,189,071 A | 6/1965 | Balkema et al. | |
| 3,494,496 A * | 2/1970 | Livingstone | B65D 41/185 |
| | | | 215/320 |
| 3,592,349 A | 7/1971 | Baugh | |
| 4,712,699 A * | 12/1987 | Lutz | B65D 41/0414 |
| | | | 215/307 |
| 4,726,484 A | 2/1988 | Lutz | |
| 6,041,953 A * | 3/2000 | Goodall | B65D 41/0414 |
| | | | 215/354 |
| 6,336,571 B1 | 1/2002 | Chibret et al. | |
| 2005/0252876 A1 | 11/2005 | Albers | |
| 2006/0081655 A1 | 4/2006 | Beranger et al. | |
| 2007/0175853 A1 | 8/2007 | Kebben | |
| 2010/0025354 A1 * | 2/2010 | Hansen | B65D 47/18 |
| | | | 215/47 |
| 2011/0125111 A1 | 5/2011 | Chibret et al. | |
| 2011/0297703 A1 * | 12/2011 | Wilson | B65D 47/18 |
| | | | 222/212 |
| 2012/0296291 A1 | 11/2012 | Painchaud et al. | |
| 2014/0231536 A1 | 8/2014 | Julia et al. | |

FOREIGN PATENT DOCUMENTS

| | | |
|---|---|---|
| CH | 597049 A5 | 3/1978 |
| CN | 1277589 A | 12/2000 |
| CN | 102112377 A | 6/2011 |
| DE | 8136435 U1 | 4/1982 |
| DE | 19514457 A1 | 10/1996 |
| DE | 10160362 A1 | 6/2003 |
| FR | 2100457 A5 | 3/1972 |
| FR | 2980378 A1 | 3/2013 |
| JP | H08509935 A | 10/1996 |
| JP | 2006502063 A | 1/2006 |
| JP | 2011240989 A | 12/2011 |
| JP | 2013509220 A | 3/2013 |
| WO | 9429181 A1 | 12/1994 |

* cited by examiner

LIQUID DISPENSING DEVICE

FIELD OF THE INVENTION

The present invention relates to the dispensing of liquid, more particularly to the dispensing in the pharmaceutical field of, for example, ophthalmic, nasal, buccal or auricular liquid. The term "liquid product" is intended to mean a non-solid and non-gaseous product which is more or less viscous.

BACKGROUND OF THE INVENTION

Dispensing devices comprising a liquid storage reservoir and a dispensing end piece attached to a neck of the reservoir, for example by screwing, are already known, in particular from patent application FR2980378. The reservoir and the dispensing end piece are made of plastic. To ensure liquid sealing of the device, a part of the dispensing end piece is intended to come into leaktight contact with the internal surface of the neck of the reservoir so as to create a sealing zone. This contact can be achieved by an annular bead on the reservoir, or alternatively by face-to-face contact.

It is found that screwing the dispensing end piece onto the neck of the reservoir is carried out at a high speed (for example greater than 300 rotations per minute), which can generate chips of material resulting from friction between the dispensing end piece and the neck of the reservoir at the sealing zone. These chips risk falling into the liquid contained in the reservoir and contaminating it, or else disturbing the operation of the dispensing end piece. This phenomenon is not desirable, especially when the liquid is pharmaceutical liquid.

SUMMARY OF THE INVENTION

The present invention aims to provide a dispensing device ensuring better conservation and better dispensing of the liquid.

Accordingly, a subject of the invention is a liquid dispensing device comprising a dispensing end piece and a neck of a reservoir for storing the liquid, the dispensing end piece being attached to the neck, the neck having an internal surface of substantially tubular general shape, the dispensing end piece having an internal skirt of substantially tubular general shape which is mounted inside the neck of the reservoir and which defines, with the internal surface of the neck, at least one annular sealing zone such that liquid present in the reservoir cannot pass between the internal skirt of the dispensing end piece and the neck of the reservoir, the internal skirt of the dispensing end piece defining, with the internal surface of the neck, a separate chips retention zone arranged upstream of the sealing zone with respect to the reservoir, this retention zone being configured such that chips formed at the sealing zone while the dispensing end piece is being assembled on the neck of the reservoir cannot get into the reservoir.

Thanks to the chips retention zone, it is possible to block all the particles which may be created during assembly, resulting from friction between the interior of the reservoir and the end piece, and therefore to avoid a situation in which these particles fall into the reservoir and contaminate the liquid contained in the reservoir, or else impair the operation of the dispensing end piece, for example by clogging channels. Thus, the chips retention zone forms a barrier arranged between the sealing zone and the reservoir to retain any chips which might be formed when the internal surface of the neck of the reservoir is docked with the internal skirt of the dispensing end piece.

It will be noted that the dispensing end piece can be assembled on the neck of the reservoir in various ways, in particular by screwing, force-fitting, or else by snap-fastening. The retention zone is particularly advantageous in the case where assembly of the dispensing end piece on the reservoir is carried out in a very rapid manner, quite particularly during a screwing operation at high speed, for example greater than 300 rotations per minute. Specifically, during rapid assembly, more chips may be formed at the sealing zone since the material does not have time to deform to compensate for the tightening that generates the sealing zone. It will be understood that in the advantageous case where the dispensing end piece is attached to the neck by screwing, to ensure this screwing, the dispensing end piece comprises a threaded surface and the neck of the reservoir comprises a complementary tapped surface.

It will be noted that the dispensing device is particularly advantageous since it could have been envisioned, alternatively, to make changes to the materials for producing the reservoir and the dispensing end piece. Nevertheless, the results obtained with the device presented above are more advantageous for avoiding chips. Specifically, for example when using a polypropylene bottle, we get a more rigid bottle which is more difficult to use and whose cost is higher.

It will be noted moreover that the chips retention zone is separate from the sealing zone. Specifically, this retention zone has the function of being interposed between the reservoir and the sealing zone where chips risk being created, and therefore does not have the primary function of providing liquid sealing, even though it is not excluded from being able to do so. The term "chips retention zone separate from the sealing zone" is understood to mean the fact that the juxtaposition of the two zones is different from an exactly cylindrical and plane surface. Moreover, the term "chips" is understood to mean particles of any form which may be created by the dispensing end piece and/or the reservoir during assembly of the two parts, in particular by screwing. The chips are for example in the form of filaments or dust.

The invention may additionally comprise one or more of the following features, taken alone or in combination.

The internal surface of the neck of the reservoir has a general diameter and it comprises a convex annular shape projecting from the internal surface of the neck so as to define a reduced diameter with respect to the general diameter of the neck of the reservoir and thus to form, by cooperation with the internal skirt of the dispensing end piece, the chips retention zone. Thus, a protuberance forming an inflection is produced on the internal surface of the neck so as to retain chips resulting from screwing the dispensing end piece onto the reservoir. Preferably, the convex annular shape has a gentle inflection with respect to the internal surface of the neck in order not to create new chips at the chips retention zone during the contact which is produced. Moreover, the reduced diameter is preferably smaller than the diameter of the neck of the reservoir at the sealing zone. It will be noted that it is particularly advantageous to produce these variations in diameter on the internal surface of the neck of the reservoir rather than on the internal skirt of the dispensing end piece, since it can facilitate assembly of the two parts.

The device is configured such that, when assembling the dispensing end piece on the neck of the reservoir, the internal skirt of the dispensing end piece comes into contact with the internal surface of the neck of the reservoir first at the sealing zone and then at the chips retention zone. Thus, the contact of the retention zone takes place at the end of assembly, during which moment the assembly force is smaller, in particular the screwing torque during assembly by screwing. Thus, chips are not created between the internal surface of the neck of the reservoir and the skirt of the dispensing end piece at the chips retention zone. Furthermore, the formation of the sealing zone takes place as a priority, thereby ensuring that this sealing zone will be formed whatever the manufacturing tolerances of the parts.

The neck of the reservoir has a length $L_{neck\ min}$ delimited by the upper end of the length of the neck providing sealing $L_{neck\ sealing}$ and the upper end of the length of the neck providing the chips retention zone $L_{neck\ retention}$, the dispensing end piece has a length $L_{end\ piece\ max}$ delimited by the lower end of the length of the end piece providing sealing $L_{end\ piece\ sealing}$ and the lower end of the length of the end piece providing the chips retention zone $L_{end\ piece\ retention}$, the device being such that $L_{neck\ min} > L_{end\ piece\ max}$. By virtue of this configuration, when assembling the dispensing end piece on the neck of the reservoir, the internal skirt of the dispensing end piece comes into contact with the internal surface of the neck of the reservoir first at the sealing zone and then at the chips retention zone.

The internal surface of the neck of the reservoir at the sealing zone is substantially plane, sealing with the internal skirt of the dispensing end piece being realized by face-to-face contact of the internal skirt of the dispensing end piece with the internal surface of the neck of the reservoir. The term "face-to-face contact" is here understood to mean any type of sealing contact produced between two plane surfaces of revolution, such as a cylinder-against-cylinder contact, a cylinder-against-cone contact and a cone-against-cone contact. It will be noted that in the case of such a face-to-face contact to produce sealing, the assembly force may be relatively high since the friction surface is greater. However, as the contact is produced progressively, the risk of creating chips is reduced.

The internal surface of the neck of the reservoir at the sealing zone comprises an annular bead.

The internal surface of the neck of the reservoir comprises, downstream and in the direct vicinity of the sealing zone, an annular recess. This recess allows the contact surface in the sealing zone to be as localized as possible, so as to create fewer chips. Furthermore, this recess makes it possible to produce an upper part of the neck having a minimal thickness and capable of forming a stop with the bottom of a groove formed by the internal skirt of the dispensing end piece. As this thickness is minimal, the stop between the top of the neck of the reservoir and the bottom of this groove is more clearly defined, thereby making it possible to create a second liquid sealing zone which is particularly effective.

The neck of the reservoir is made of low density polyethylene and the internal skirt of the dispensing end piece is made of high density polyethylene. Thus, the reservoir is made of a flexible material, enabling the liquid to be readily dispensed by pressure exerted by the user, and the dispensing end piece is made of a more rigid material, thereby making it possible to facilitate the assembly of the parts and to ensure an effective sealing of the dispensing device. In this case, the chips are mainly created on the reservoir and the retention zone proposed in the present device is particularly advantageous.

The end of the internal skirt of the dispensing end piece situated on the side facing the reservoir has a funnel shape. This has the effect of facilitating assembly of the dispensing end piece with the reservoir.

Another subject of the invention is a liquid storage reservoir for a device as described above, in which the internal surface of the neck of the reservoir has a predetermined diameter at the sealing zone, referred to as sealing diameter, and a predetermined diameter at the retention zone, referred to as chips retention diameter, the chips retention diameter being smaller than the sealing diameter.

A further subject of the invention is a method for assembling a device as described above, during which the internal skirt of the dispensing end piece comes into contact with the internal surface of the neck of the reservoir first at the sealing zone and then at the chips retention zone.

BRIEF DESCRIPTION OF THE DRAWINGS

The invention will be better understood on reading the following description given solely by way of example with reference to the drawings, in which.

DETAILED DESCRIPTION OF THE INVENTION

Figure 1:
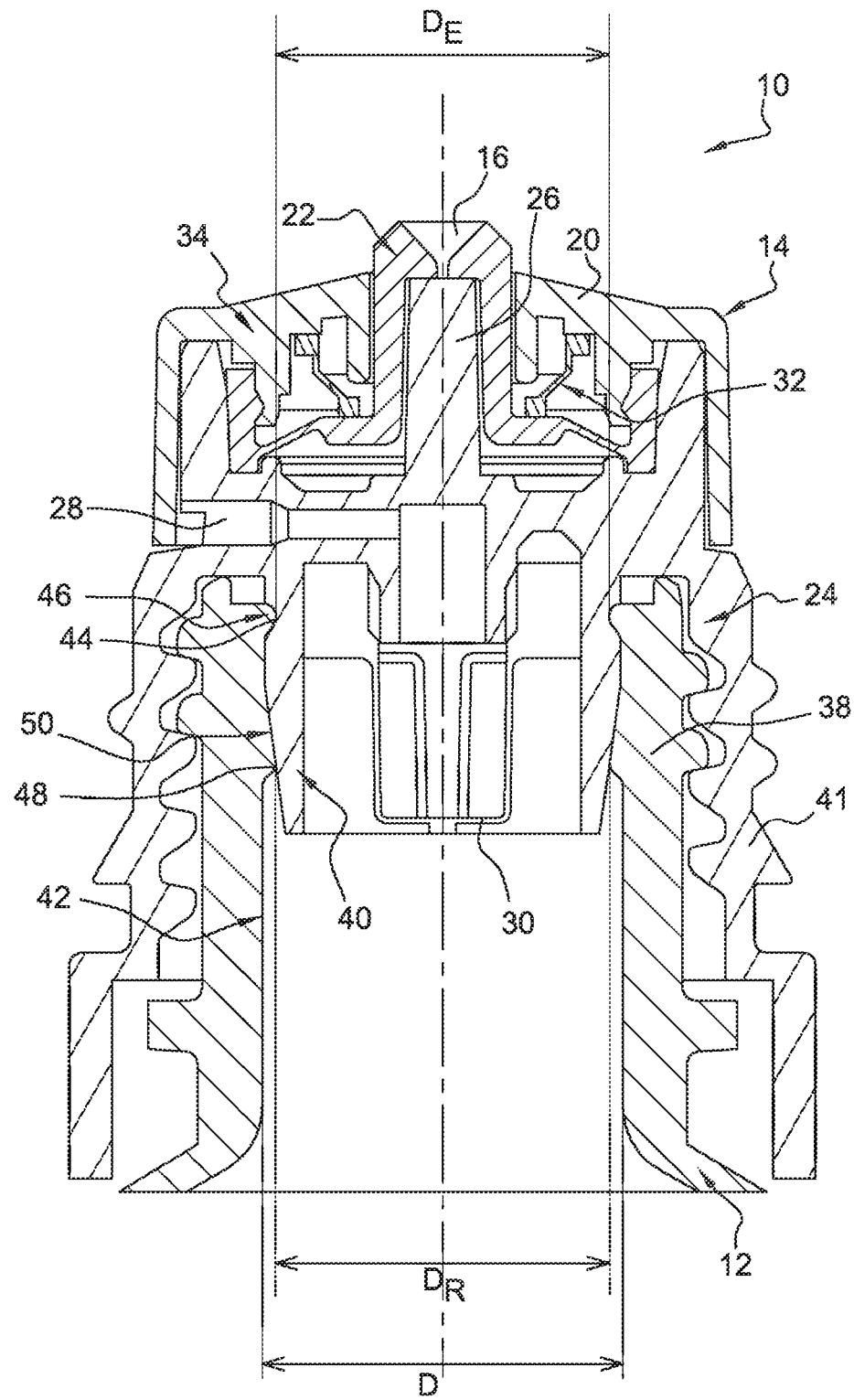
FIG. 1 is a sectional view in longitudinal direction of a device according to a first embodiment.

FIG. 1 illustrates a device 10 for dispensing liquid in the form of drops that comprises a reservoir 12 to which is attached a dispensing end piece 14 over which a protective cap 18 (visible in FIG. 2 or FIG. 3) can be mounted. The reservoir 12 comprises a neck 38 for receiving the dispensing end piece 14.

The dispensing end piece 14 has an upper dispensing end 20 in which an orifice 16 is formed for dispensing calibrated drops, in this example, by drops formation means 16. More precisely, again in this example, the dispensing end piece 14 is of substantially cylindrical general shape. The dispensing end piece 14 here comprises a drop dispensing valve 22 made of elastomer material so as to take, under the pressure of the liquid (when the user presses on the reservoir 12), a liquid passage configuration. The dispensing end piece 14 further comprises a valve support 24, attached to the reservoir 12, bearing a pin 26 forming a seat against which the valve 22 is pressed and also comprising an air passage duct 28 shut off by an air-permeable member 30 preventing bacteria from entering into the reservoir 12. The dispensing end piece 14 also comprises a return element 32 allowing the valve 22 to be returned into a liquid blocking configuration. Finally, the dispensing end piece 14 comprises a cover 34 for pressing the valve 22 against the support 24.

More precisely, the valve support 24 comprises an internal skirt 40 of substantially tubular general shape, which is mounted inside the neck 38 of the reservoir 12, and also an external skirt 41 surrounding the neck 38 of the reservoir 12 and having, for example, a tapped surface for screwing the dispensing end piece 14 onto the reservoir 12. The tapped surface is situated on the inner side of the external skirt 41. The internal skirt 40 has a lower end of funnel shape in order to facilitate the insertion of the dispensing end piece 14 into the neck 38 of the reservoir 12. In the device 10 of FIG. 1, the neck 38 has a substantially tubular internal surface 42 having a general diameter and comprising an annular bead 44. The annular bead 44 forms a sealing zone 46 with the internal skirt 40 of the dispensing end piece 14. When screwing the dispensing end piece 14, the internal skirt 40 comes into contact with the annular bead 44 at a high speed, which can generate chips of plastics material, for example in the form of filaments, which risk falling into the reservoir 12 and contaminating the liquid contained in the reservoir 12.

The internal surface 42 of the neck 38 further comprises a convex annular shape 48 projecting from the internal surface 42 of the neck 38 so as to define a reduced diameter with respect to the general diameter, referred to as chips retention diameter $D_R$, represented in FIG. 1. This chips retention diameter $D_R$ is smaller than the general diameter D of the neck 38 of the reservoir 12, and also smaller than the diameter $D_E$ of the neck 38 of the reservoir 12 at the sealing zone 46, referred to as sealing diameter $D_E$. This convex shape 48 produces, by cooperation with the internal skirt 40 of the dispensing end piece 14, a chips retention zone 50. When the dispensing end piece 14 is mounted on the neck 38 of the reservoir 12, by screwing, the chips created by friction between the neck 38 and the skirt 40 in the sealing zone 46 are blocked in this chips retention zone 50 and cannot fall into the reservoir 12. It will be understood that the neck 38 of the reservoir has a threaded external surface in order to screw the dispensing end piece 14 onto the reservoir 12, by cooperation with the tapped surface of the external skirt 41.

Figure 2:
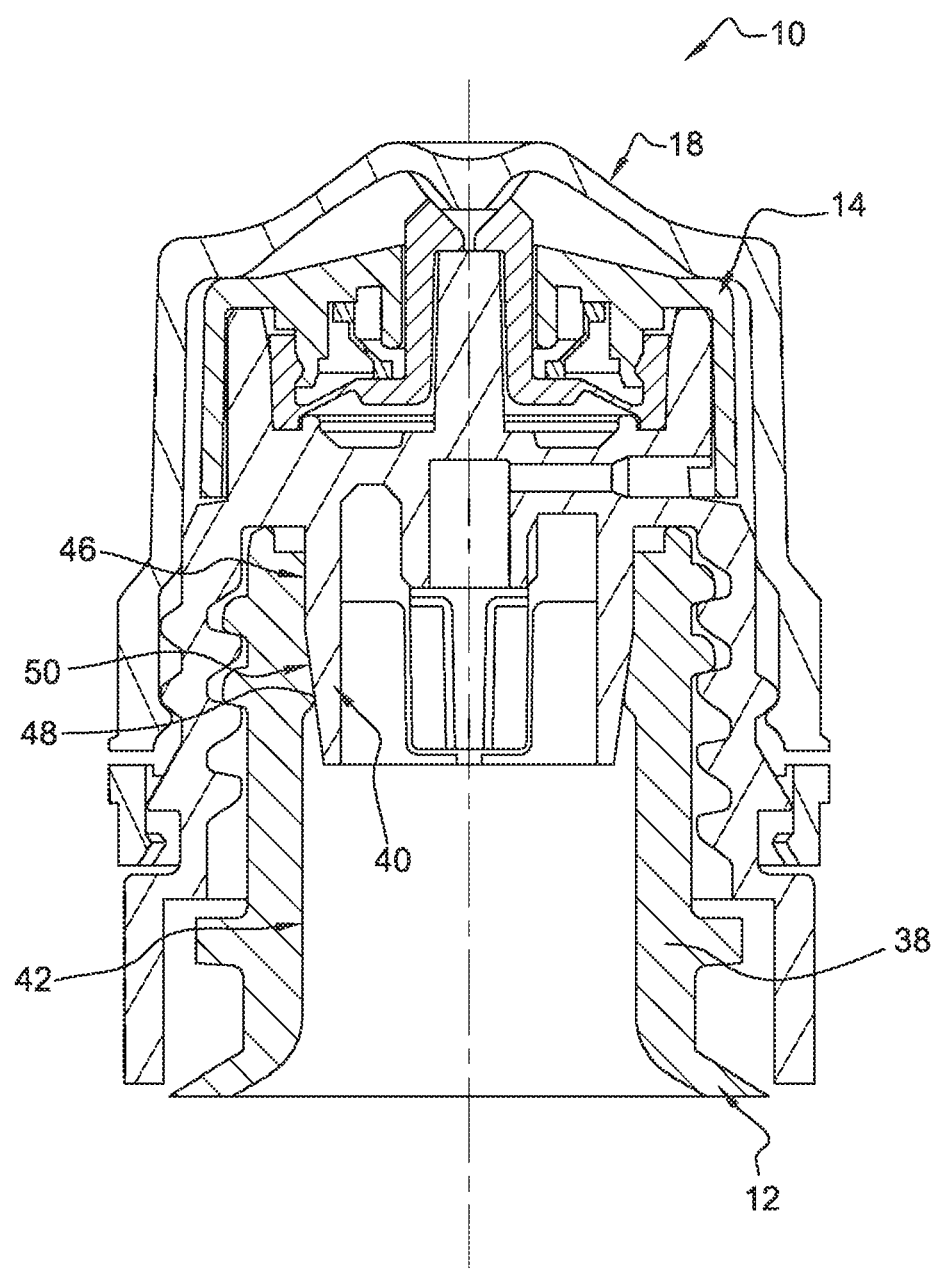
FIG. 2 is a view, similar to FIG. 1, of a device according to a second embodiment.

In the embodiment in FIG. 2, the internal surface 42 of the neck 38 does not comprise an annular bead but is substantially plane in the sealing zone 46. In this example, sealing between the internal surface 42 and the internal skirt 40 is achieved by face-to-face contact, in this instance a cylinder-against-cylinder contact of the two tubular surfaces of the skirt 40 and the internal surface 42. The internal surface 42 of the neck 38 also comprises a convex annular shape 48 projecting from the internal surface 42 so as to form, by cooperation with the internal skirt 40 of the dispensing end piece 14, a chips retention zone 50. In this case, the contact surface is more extensive, without pointed contact, the risk of creating chips is thus reduced.

Figure 3:
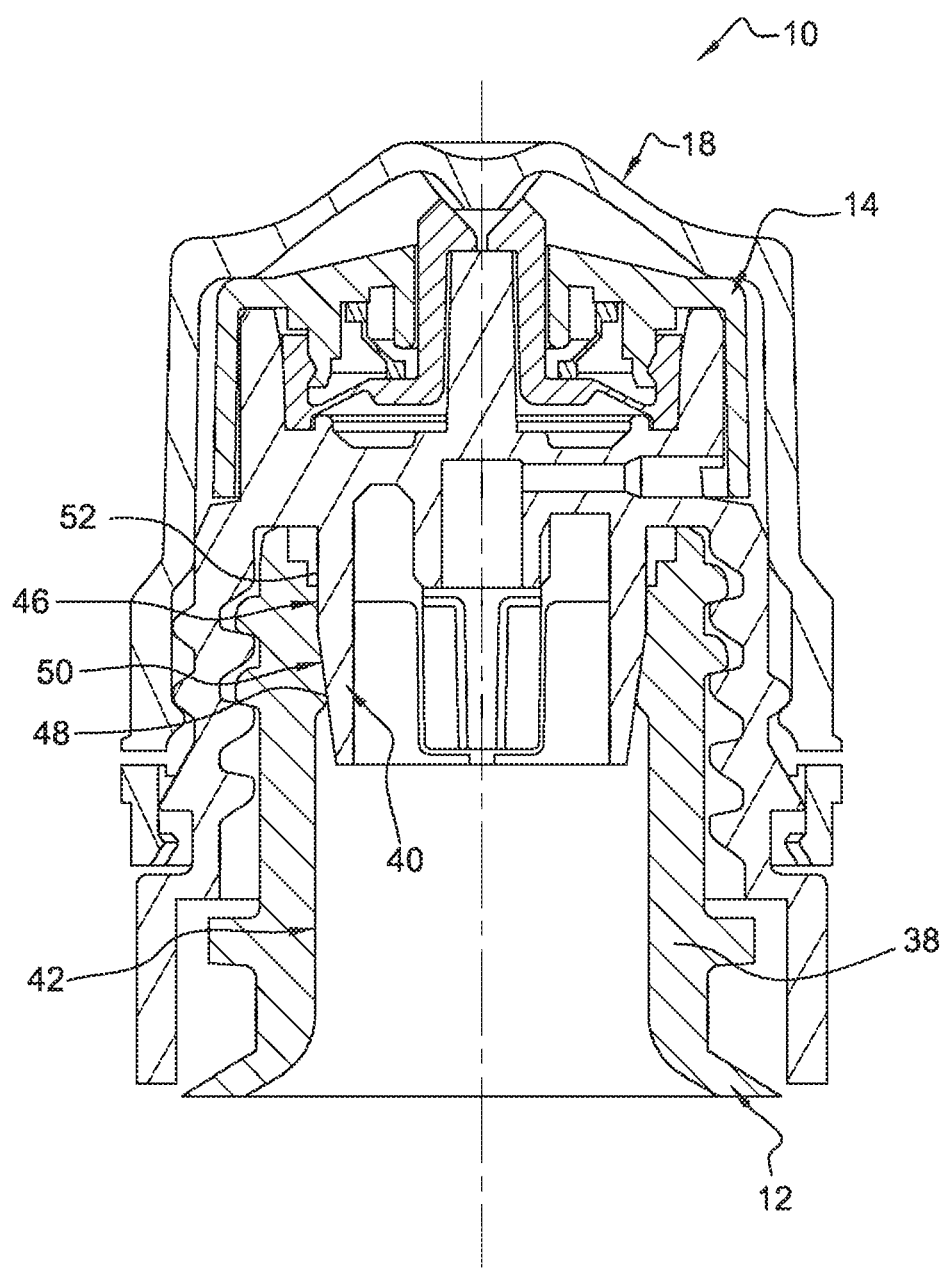
FIG. 3 is a view, similar to FIG. 1, of a device according to a third embodiment.

In FIG. 3, sealing between the internal surface 42 and the internal skirt 40 is also provided by cylinder-against-cylinder contact. Unlike the example illustrated in FIG. 2, the internal surface 42 of the neck 38 comprises, downstream and in the direct vicinity of the sealing zone 46, an annular recess 52. As the chips are created in the sealing zone 46, it is preferable that the contact surface in the sealing zone 46 is as localized as possible. Thus, the screwing torque will be reduced and fewer chips will be created.

Figure 4:
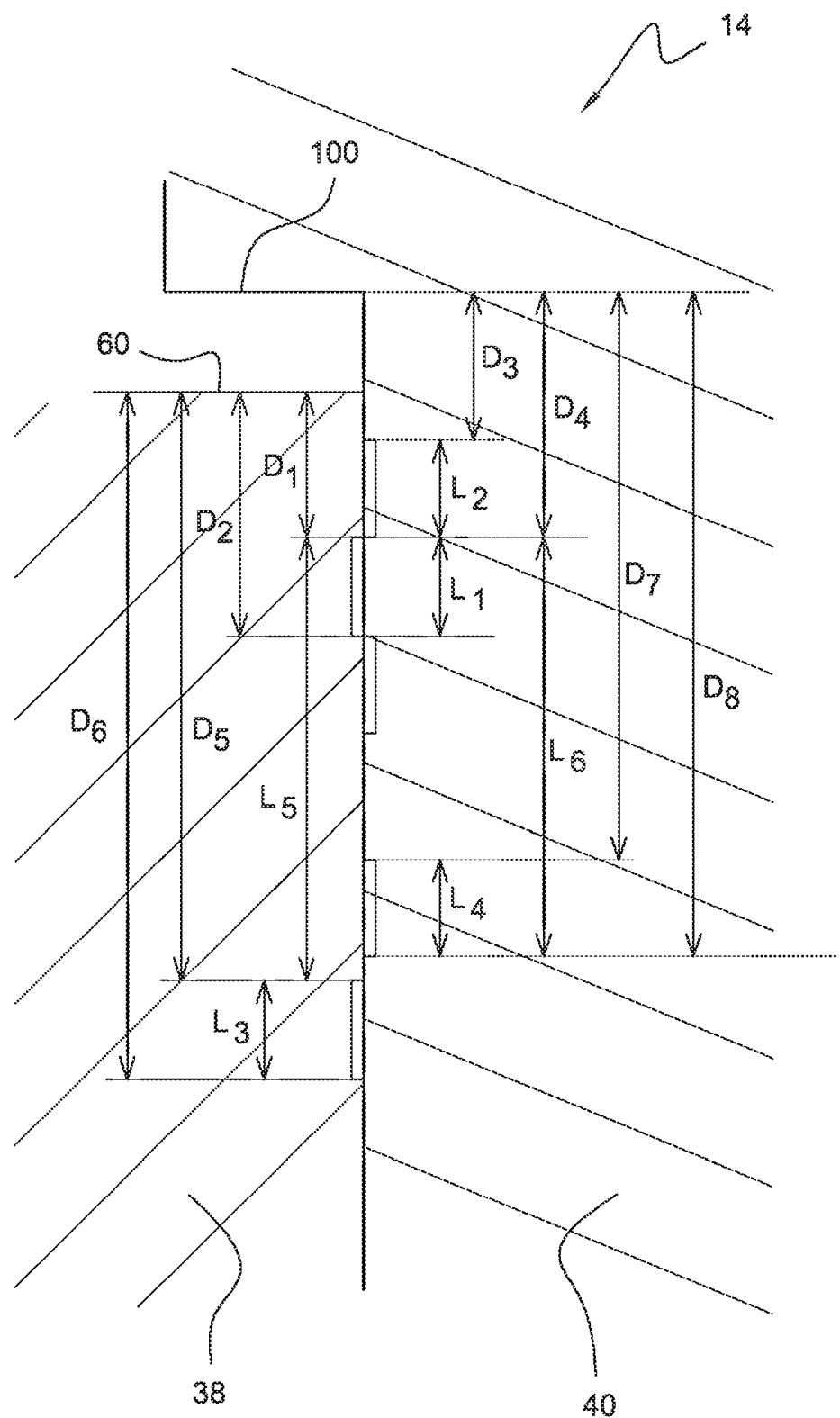
FIG. 4 is a schematic view illustrating the relative positions of the sealing zones and the chips retention zones.

When assembling the dispensing end piece 14 on the reservoir 12, the internal skirt 40 is inserted into the neck 38 of the reservoir 12 and the contact with the retention zone 50 takes place after contact with the sealing zone 46. In order to illustrate the configuration of the parts to ensure this order of contact, a schematic view illustrating the relative positions of the sealing zones 46 and the chips retention zones 50 is represented in FIG. 4.

The internal surface 42 of the neck 38 and the internal skirt 40 each have a theoretical length in the longitudinal direction $L1=L_{neck\ theoretical\ sealing}$ and $L2=L_{end\ piece\ theoretical\ sealing}$ which are intended to provide sealing, producing the sealing zone 46.

The theoretical length of the neck 38 $L1=L_{neck\ theoretical\ sealing}$ defines, with reference to the upper end 60 of the neck 38, a minimum theoretical distance $D1=D_{neck\ theoretical\ sealing\ min}$ and a maximum theoretical distance $D2=D_{neck\ theoretical\ sealing\ max}$.

The theoretical length of the dispensing end piece 14 $L2=L_{end\ piece\ theoretical\ sealing}$ defines, with respect to the bottom of the groove 100 of the dispensing end piece 14, a minimum theoretical distance $D3=D_{end\ piece\ theoretical\ sealing\ min}$ and a maximum theoretical distance $D4=D_{end\ piece\ theoretical\ sealing\ max}$.

To ensure that there is sealing, that is to say that at least a part of the length $L1=L_{neck\ theoretical\ sealing}$ of the internal surface 42 of the neck 38 is in contact with at least a part of the length $L2=L_{end\ piece\ theoretical\ sealing}$ of the internal skirt 40 of the dispensing end piece 14, it is required that the following holds simultaneously:

i) $D1=D_{neck\ theoretical\ sealing\ min} < D_{end\ piece\ theoretical\ sealing\ max}=D4$ and that ii) $D3=D_{end\ piece\ theoretical\ sealing\ min} < D_{neck\ theoretical\ sealing\ max}=D2$.

Thus, when the end of the neck 38 and the bottom of the groove 100 of the dispensing end piece 14 are in contact, the sealing is guaranteed.

Likewise, the conditions for the chips retention zone 50 to exist can be understood. The internal surface 42 of the neck 38 and the internal skirt 40 each have a theoretical length in the longitudinal direction $L3=L_{neck\ theoretical\ retention}$ and $L4=L_{end\ piece\ theoretical\ retention}$ which are intended to provide the retention zone, producing the chips retention zone 50.

The theoretical length of the neck 38 $L3=L_{neck\ theoretical\ retention}$ defines, with reference to the upper end 60 of the neck 38, a minimum theoretical distance $D5=D_{neck\ theoretical\ retention\ min}$ and a maximum theoretical distance $D6=D_{neck\ theoretical\ retention\ max}$.

The theoretical length of the dispensing end piece 14 $L4=L_{end\ piece\ theoretical\ retention}$ defines, with reference to the bottom of the groove 100 of the dispensing end piece 14, a minimum theoretical distance $D7=D_{end\ piece\ theoretical\ retention\ min}$ and a maximum theoretical distance $D8=D_{end\ piece\ theoretical\ retention\ max}$.

To ensure that there is the retention zone, that is to say to ensure that at least a part of the length $L3=L_{neck\ theoretical\ retention}$ of the internal surface 42 of the neck 38 is in contact with at least a part of the length $L4=L_{end\ piece\ theoretical\ retention}$ of the internal skirt 40 of the dispensing end piece 14, it is required that the following holds simultaneously:

iii) $D5=D_{neck\ theoretical\ sealing\ min} < D_{end\ piece\ theoretical\ sealing\ max}=D8$ and that iv) $D7=D_{end\ piece\ theoretical\ sealing\ min} < D_{neck\ theoretical\ sealing\ max}=D6$.

Thus, when the end of the neck 38 and the bottom of the groove 100 of the dispensing end piece 14 are in contact, the chips retention zone 50 is guaranteed.

In the following, the configurations allowing the contact of the retention zone 50 to take place after the contact of the sealing zone 46 are developed.

The minimum theoretical distances on the neck $D1=D_{neck\ theoretical\ sealing\ min}$ and $D5=D_{neck\ theoretical\ retention\ min}$ define a length of the neck $L5=L_{neck\ min}$, delimited by the upper end of the theoretical length providing sealing and the upper end of the theoretical length providing the retention zone. Moreover, the maximum theoretical distances on the end piece $D4=D_{end\ piece\ theoretical\ sealing\ max}$ and $D8=D_{end\ piece\ theoretical\ retention\ max}$ define a length of the end piece $L6=L_{end\ piece\ max}$, delimited by the lower end of the theoretical length providing sealing and the lower end of the theoretical length providing the retention zone.

To ensure that the contact of the retention zone 50 takes place after the contact of the sealing zone 46, it is required that the following holds: $L5=L_{neck\ min}>L6=L_{end\ piece\ max}$.

It will be understood that a "theoretical" length denotes a predefined length on the neck of the reservoir or the dispensing end piece at the time of designing or manufacturing these parts, knowing that, due to the manufacturing tolerances, once the parts have been assembled, sealing or chips retention does not necessarily take place over the entire theoretical length, but only over a part of this length. Thus, it can be found that on the devices configured according to this embodiment the neck of the reservoir has a length $L_{neck\ min}$ delimited by the upper end of the length of the neck providing sealing $L_{neck\ sealing}$ and the upper end of the length of the neck providing the chips retention zone $L_{neck\ retention}$, the dispensing end piece has a length $L_{end\ piece\ max}$ delimited by the lower end of the length of the dispensing end piece providing sealing $L_{end\ piece\ sealing}$ and the lower end of the length of the dispensing end piece providing the chips retention zone $L_{end\ piece\ retention}$, and the device is dimensioned such that $L_{neck\ min}>L_{end\ piece\ max}$.

Figure 5:
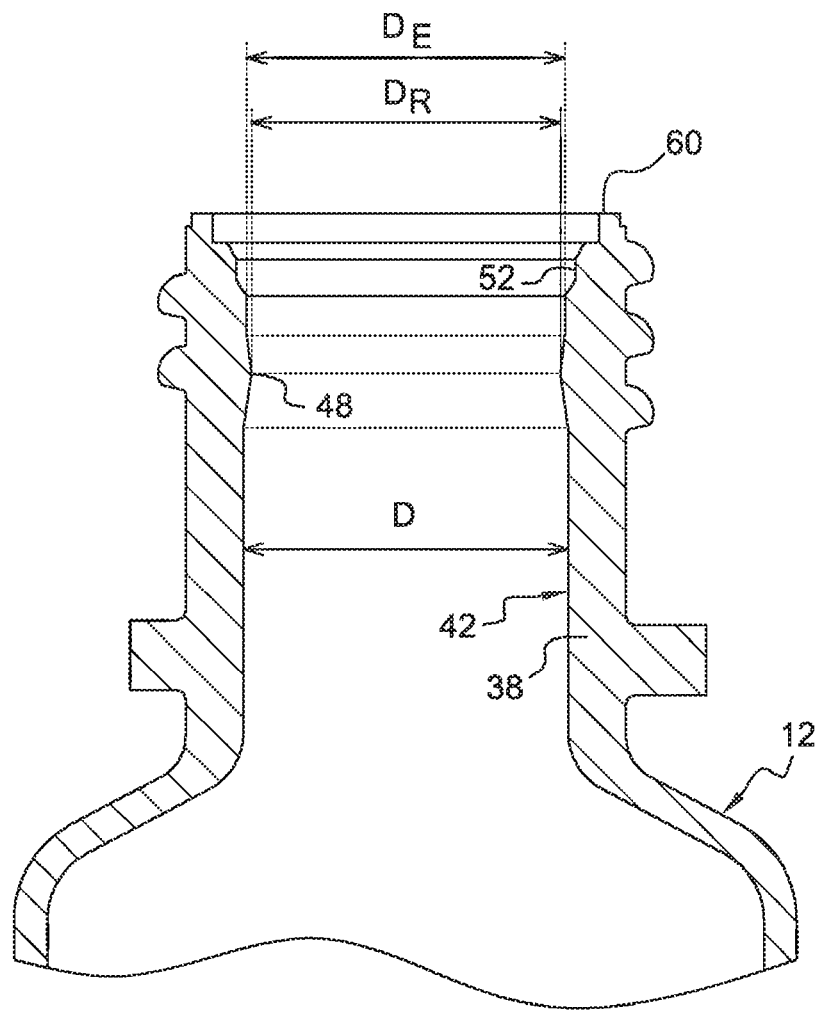
FIG. 5 is a sectional view in longitudinal direction of the reservoir of the device of FIG. 3.

As can be seen in FIG. 5, the reservoir 12 is configured such that the internal surface 42 of the neck 38 has a sealing diameter $D_E$ greater than the chips retention diameter $D_R$.

It will be noted that the neck 38 of the reservoir 12 is made, in this example, of low density polyethylene, and the internal skirt 42 of the dispensing end piece 14 is made of high density polyethylene.

It will be understood that the devices 10 described above are particularly advantageous for avoiding the presence of chips in the reservoir 12 and that the invention is not limited to the examples described above.

The invention claimed is:

1. A liquid dispensing device, characterized in that it comprises a dispensing end piece and a neck of a reservoir for storing the liquid, the dispensing end piece being attached to the neck by screwing,
the neck having an internal surface of substantially tubular general shape,
the dispensing end piece having an internal skirt which is mounted inside the neck of the reservoir and which defines, with the internal surface of the neck, at least one annular sealing zone such that liquid present in the reservoir cannot pass between the internal skirt of the dispensing end piece and the neck of the reservoir,
the internal skirt of the dispensing end piece defining, with the internal surface of the neck, a separate chips retention zone arranged upstream of the sealing zone with respect to the reservoir, the chips retention zone being configured such that chips formed at the sealing zone while the dispensing end piece is being assembled on the neck of the reservoir cannot get into the reservoir,
wherein the dispensing end piece comprises a threaded surface which engages, by screwing, with a threaded surface on the neck during mounting of the device and is not detached therefrom during normal use.

2. The device as claimed in claim 1, wherein the internal surface of the neck of the reservoir has a general diameter and it comprises a convex annular shape projecting from the internal surface of the neck so as to define a reduced diameter with respect to the general diameter of the neck of the reservoir and thus to form, by cooperation with the internal skirt of the dispensing end piece, the chips retention zone.

3. The device as claimed in claim 2, wherein the reduced diameter is smaller than the diameter of the neck of the reservoir at the sealing zone.

4. The device as claimed in claim 1, configured such that, when assembling of the dispensing end piece on the neck of the reservoir, the internal skirt of the dispensing end piece comes into contact with the internal surface of the neck of the reservoir first at the sealing zone and then at the chips retention zone.

5. The device as claimed in claim 4, wherein
the neck of the reservoir has a length ($L_{neck\ min}$) delimited by an upper end of a length of the neck providing sealing ($L_{neck\ sealing}$) and an upper end of a length of the neck providing the chips retention zone ($L_{neck\ retention}$),
the dispensing end piece has a length ($Lend_{piece\ max}$) delimited by a lower end of a length of the end piece providing sealing ($Lend_{piece\ sealing}$) and a lower end of a length of the end piece providing the chips retention zone ($Lend_{piece\ retention}$),
and wherein $L_{neck\ min}>$Lend piece max.

6. The device as claimed in claim 1, wherein the internal surface of the neck of the reservoir at the sealing zone is substantially plane, sealing with the internal skirt of the dispensing end piece being realized by face-to-face contact of the internal skirt of the dispensing end piece with the internal surface of the neck of the reservoir.

7. The device as claimed in claim 1, wherein the internal surface of the neck of the reservoir at the sealing zone comprises an annular bead.

8. The device as claimed in claim 1, wherein the internal surface of the neck of the reservoir comprises, downstream and in the direct vicinity of the sealing zone, an annular recess.

9. The device as claimed in claim 1, wherein the neck of the reservoir is made of low density polyethylene and the internal skirt of the dispensing end piece is made of high density polyethylene.

10. The device as claimed in claim 1, wherein the end of the internal skirt of the dispensing end piece situated on the side facing the reservoir has a funnel shape.

11. The device as claimed in claim 2, wherein the internal surface of the neck of the reservoir at the sealing zone comprises an annular bead.

12. The device as claimed in claim 3, wherein the internal surface of the neck of the reservoir at the sealing zone comprises an annular bead.

13. The device of claim 1, wherein the dispensing end piece has an external skirt surrounding the internal skirt, wherein the threaded surface of the dispensing end piece is on an inner side of the external skirt.

14. A liquid dispensing device, characterized in that it comprises a dispensing end piece and a neck of a reservoir for storing the liquid, the dispensing end piece being attached to the neck by screwing,
the neck having an internal surface of substantially tubular general shape,
the dispensing end piece having an internal skirt of substantially tubular general shape which is mounted inside the neck of the reservoir and which defines, with the internal surface of the neck, at least one annular sealing zone such that liquid present in the reservoir cannot pass between the internal skirt of the dispensing end piece and the neck of the reservoir, the internal skirt of the dispensing end piece defining, with the internal surface of the neck, a separate chips retention zone arranged upstream of the sealing zone with respect to the reservoir, the chips retention zone being configured such that chips formed at the sealing zone while the dispensing end piece is being assembled on the neck of the reservoir cannot get into the reservoir, wherein the dispensing end piece has a threaded surface which engages, by screwing, with a threaded surface on the neck during mounting of the device and is not detached therefrom during normal use.

\* \* \* \* \*

UNITED STATES PATENT AND TRADEMARK OFFICE
CERTIFICATE OF CORRECTION

Page 1 of 1

PATENT NO. : 11,242,181 B2
APPLICATION NO. : 15/301606
DATED : February 8, 2022
INVENTOR(S) : Thierry Decock et al.

It is certified that error appears in the above-identified patent and that said Letters Patent is hereby corrected as shown below:

On the Title Page

Item [72], Line 1:
"Thierry Decock, Lyons (FR)"
Should be changed to:
"Thierry Decock, Lyon (FR)"

Item [72], Line 2:
"Benjamin Quaglia, Lyons (FR)"
Should be changed to:
"Benjamin Quaglia, Lyon (FR)"

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*